*US010035958B2*

(12) United States Patent
Medoff

(10) Patent No.: US 10,035,958 B2
(45) Date of Patent: *Jul. 31, 2018

(54) PROCESSING MATERIALS

(71) Applicant: XYLECO, INC., Wakefield, MA (US)

(72) Inventor: Marshall Medoff, Brookline, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/451,166

(22) Filed: Mar. 6, 2017

(65) Prior Publication Data

US 2017/0175007 A1    Jun. 22, 2017

Related U.S. Application Data

(60) Division of application No. 14/722,577, filed on May 27, 2015, now Pat. No. 9,624,443, which is a continuation of application No. 14/074,258, filed on Nov. 7, 2013, now Pat. No. 9,074,142, which is a continuation of application No. 12/605,534, filed on Oct. 26, 2009, now Pat. No. 8,597,472.

(60) Provisional application No. 61/109,159, filed on Oct. 28, 2008.

(51) Int. Cl.

| C10G 15/10 | (2006.01) |
| C10G 15/00 | (2006.01) |
| C10L 9/00 | (2006.01) |
| C10G 1/04 | (2006.01) |
| C10G 1/00 | (2006.01) |
| C10G 9/24 | (2006.01) |
| C10G 1/02 | (2006.01) |
| C10G 57/00 | (2006.01) |
| C10G 11/00 | (2006.01) |
| C10G 32/00 | (2006.01) |
| C10G 51/02 | (2006.01) |
| C10G 55/02 | (2006.01) |
| C12P 7/06 | (2006.01) |
| C10G 47/12 | (2006.01) |
| C10G 15/08 | (2006.01) |
| C10L 1/02 | (2006.01) |
| C10G 5/00 | (2006.01) |
| C10G 51/04 | (2006.01) |
| C10G 55/04 | (2006.01) |

(52) U.S. Cl.
CPC .............. *C10G 15/10* (2013.01); *C10G 1/00* (2013.01); *C10G 1/002* (2013.01); *C10G 1/02* (2013.01); *C10G 1/04* (2013.01); *C10G 9/24* (2013.01); *C10G 11/00* (2013.01); *C10G 15/00* (2013.01); *C10G 32/00* (2013.01); *C10G 51/02* (2013.01); *C10G 55/02* (2013.01); *C10G 57/005* (2013.01); *C10L 9/00* (2013.01); *H05K 999/99* (2013.01); *C10G 5/00* (2013.01); *C10G 15/08* (2013.01); *C10G 47/12* (2013.01); *C10G 51/04* (2013.01); *C10G 55/04* (2013.01); *C10G 2300/1011* (2013.01); *C10G 2300/1014* (2013.01); *C10G 2300/1025* (2013.01); *C10G 2300/1033* (2013.01); *C10L 1/02* (2013.01); *C12P 7/06* (2013.01); *Y02E 50/17* (2013.01); *Y02P 30/20* (2015.11)

(58) Field of Classification Search
CPC ...... C10G 15/10; C10G 15/00; C10G 57/005; C10G 55/02; C10G 51/02; C10G 11/00; C10G 32/00; C10G 1/04; C10G 1/00; C10G 2300/1011; C12P 7/06
See application file for complete search history.

(56) References Cited

U.S. PATENT DOCUMENTS

| 2,955,997 | A | 10/1960 | Allen et al. |
| 3,090,698 | A | 5/1963 | Wilson |
| 3,849,287 | A | 11/1974 | Gleim et al. |
| 3,870,611 | A | 3/1975 | Vestal |
| 3,945,679 | A | 3/1976 | Closmann |
| 3,982,995 | A | 9/1976 | Yen |
| 4,011,153 | A * | 3/1977 | Fu ............................ C10G 1/00 208/422 |
| 4,081,250 | A | 3/1978 | Hsu et al. |
| 4,092,235 | A | 5/1978 | Schlosberg et al. |
| 4,152,120 | A | 5/1979 | Zavitsanos et al. |
| 4,279,722 | A | 7/1981 | Kirkbride |
| 4,371,481 | A | 2/1983 | Pollock |
| 4,406,762 | A | 9/1983 | Ray et al. |

(Continued)

FOREIGN PATENT DOCUMENTS

| BE | 546729 | 10/1959 |
| GB | 866752 | 4/1961 |

(Continued)

OTHER PUBLICATIONS

English abstract of JP 2005232259A, dated Sep. 2005. (Year: 2005).*
Baker-Jarvis et al., "Mathematical model for in situ oil shale retorting by electromagnetic radiation," Fuel, IPC Science and Technology Press, GB, vol. 67, No. 7, Jul. 1, 1988, pp. 916-926, XP023632072 ISSN.
Moroz et al., "Optical Alteration of Complex Organics Induced by Ion Irradiation: 1. Laboratory Experiments Suggest Unusual Space Weathering Trend," Icarus, Elsevier, [Online] vol. 170, Mar. 24, 2004, pp. 214-228, XP002557447.

(Continued)

*Primary Examiner* — Renee Claytor
*Assistant Examiner* — Susan E. Fernandez
(74) *Attorney, Agent, or Firm* — Leber IP Law; Shelly M. Fujikawa

(57) ABSTRACT

Biomass (e.g., plant biomass, animal biomass, and municipal waste biomass) is processed to produce useful products, such as fuels. For example, systems are described that can use feedstock materials, such as cellulosic and/or lignocellulosic materials and/or starchy materials, to produce ethanol and/or butanol, e.g., by fermentation. Hydrocarbon-containing materials are also used as feedstocks.

25 Claims, 4 Drawing Sheets

(56) References Cited

U.S. PATENT DOCUMENTS

| | | | |
|---|---|---|---|
| 4,424,169 A | 1/1984 | Swedo | |
| 4,574,038 A | 3/1986 | Wan | |
| 4,769,082 A | 9/1988 | Kumakura et al. | |
| 4,939,360 A * | 7/1990 | Sakai | H01J 37/026 250/251 |
| 4,944,936 A | 7/1990 | Lawhorne | |
| 5,181,998 A | 1/1993 | Murphy et al. | |
| 5,393,311 A | 2/1995 | Marhanka | |
| 5,417,824 A | 5/1995 | Greenbaum | |
| 5,541,096 A | 7/1996 | Nomura | |
| 5,670,345 A | 9/1997 | Srivastava et al. | |
| 5,719,274 A | 2/1998 | Doenges et al. | |
| 5,722,927 A | 3/1998 | Fuchs et al. | |
| 5,916,780 A | 6/1999 | Foody et al. | |
| 6,315,871 B1 * | 11/2001 | Daulton | C30B 1/00 204/157.47 |
| 6,592,723 B2 | 7/2003 | Cha | |
| 8,025,098 B2 | 9/2011 | Medoff | |
| 8,534,351 B2 | 9/2013 | Medoff | |
| 9,074,142 B2 | 7/2015 | Medoff | |
| 2002/0166794 A1 | 11/2002 | Bronshtein | |
| 2003/0042172 A1 | 3/2003 | Sharivker et al. | |
| 2006/0265953 A1 | 11/2006 | Hobbs | |
| 2008/0114468 A1 | 5/2008 | Kumar | |
| 2009/0308789 A1 | 12/2009 | Al-Sheikhly | |
| 2010/0247853 A1 | 9/2010 | Ichikawa | |

FOREIGN PATENT DOCUMENTS

| | | | |
|---|---|---|---|
| JP | S36-9964 | 7/1961 | |
| JP | S63-133997 | 6/1988 | |
| JP | 06-287567 | 10/1994 | |
| JP | 2005232259 | 9/2005 | |
| JP | 2005232259 A * | 9/2005 | |
| RU | 2099317 | 12/1997 | |
| WO | WO-9535148 A1 * | 12/1995 | B01D 53/52 |
| WO | 2002002288 | 1/2002 | |
| WO | 2008009644 | 1/2008 | |
| WO | 2008014526 | 1/2008 | |
| WO | 2009134736 | 11/2009 | |
| WO | 2009134746 | 11/2009 | |
| WO | 2009134764 | 11/2009 | |
| WO | 2009134816 | 11/2009 | |
| WO | 2009154876 | 12/2009 | |
| WO | 2009155337 | 12/2009 | |

OTHER PUBLICATIONS

W.M. Haynes, ed., CRC Handbook of Chemistry and Physics, 92nd Edition (Internet Version 2012), [online]. CRC Press/Taylor and Francis, Boca Raton, FL [retrieved on Dec. 14, 2011], pp. 4-43, 4-69, 4-96, 12-212, 12-213.
Serway, RA. Physics for Scientists and Engineers, vol. II, Fourth edition, Philadelphia, Saunders College Publishing 1996, pp. 1151 and 1173-1175.
Perry, R.H,; Green, D.W. (1997) Perry's Chemical Engineers' Handbook (7th Edition). [online], (pp. 2-161, 2-163, 2-168).
Mehnert, R. Electron beams in research and technology, Nuclear Instruments and Methods in Physics Research B, 1995, 105: 348-358.
Kumakura M. and Isao Kaetsu, Radiation-Induced Decomposition and Enzymatic Hydrolysis of Cellulose, Biotechnology and Bioengineering, 1978, 20(8), 1309-1315.
Kumakura, M. and Isao Kaetsu, Heat Enhancement Effects in Radiation Pretreatment of Cellulosic Wastes, Ind. Eng. Chem. Prod. Res. Dev. 1984, 23: 88-91.
Eurasian Search Report, Corresponding Eurasian Application No. 201500171, dated May 30, 2015, 2 pages.
W.M. Yao et al., "Passage of Particles Through Matter", Journal of Physics G, vol. 33, 2006, pp. 1-34.
M.R. Cleland, "Industrial Applications of Electron Accelerators", Industrial Applications of Electron Accelerators, 2006, pp. 383-416.
V.J. Linnenbom, "Range-Energy Relations for Protons and Electrons in Al, Si, and SiO2", Radiation Effects Branch, Radiation Division, U.S. Naval Research Laboratory, Sep. 28, 1962, 19 pages.
K.E. Holbert, "Charged Particle Ionization and Range", EEE 460-Handout, Feb. 27, 2012, 6 pages.
Hegelich, B.M. et al., "Laser Acceleration of Quasi-Monoenergetic MeV Ion Beams", Nature, vol. 439, Jan. 26, 2006, pp. 441-444.
W.M. Haynes, ed. CRC Handbook of Chemistry and Physics, 96th edition (Internet Version 2016). [online], CRC Press/Taylor and Francis, Boca Raton, FL [retrieved on Dec. 1, 2015], pp. 4-96, 5-4, 5-17, and 12-215.
Office Action—Corresponding Japanese Application No. 2016-150987, dated May 16, 2018, 6 pages.

* cited by examiner

PROCESSING MATERIALS

RELATED APPLICATIONS

This application is a divisional of U.S. application Ser. No. 14/722,577, filed May 27, 2015, which is a continuation of U.S. application Ser. No. 14/074,258, filed Nov. 7, 2013, now U.S. Pat. No. 9,074,142, granted on Jul. 7, 2015, which is a continuation of U.S. application Ser. No. 12/605,534, filed Oct. 26, 2009, now U.S. Pat. No. 8,597,472, granted on Dec. 3, 2013, which claims the benefit of U.S. Provisional Application No. 61/109,159, filed Oct. 28, 2008. The complete disclosure of each of these applications is hereby incorporated by reference herein.

BACKGROUND

Biomass, particularly biomass waste, is abundantly available. It would be useful to derive materials and fuel, such as ethanol, from biomass and other materials.

SUMMARY

Materials can be processed to alter their structure at one more levels. The processed materials can then be used as a source of other materials and fuel.

Many embodiments of this application use Natural Force™ Chemistry (NFC). Natural Force™ Chemistry methods use the controlled application and manipulation of physical forces, such as particle beams, gravity, light, etc., to create intended structural and chemical molecular change. By applying the processes of Nature, new useful matter can be created without harmful environmental interference. The present application describes new feedstock preparation methods that include combining inorganic additives with materials, such as biomass, hydrocarbons or coal, to modulate, e.g., enhance, the effect on the biomass of various physical forces, such as particle beams and other forms of radiation.

Methods described herein for changing a molecular and/or a supramolecular structure of any biomass material include treating the biomass material with radiation after the addition of inorganic additives, such as one or more ceramics, and/or one or more metals, and/or one or more refractive materials, and/or one or more clays, and/or one or more minerals. In particular, the radiation can include beams of particles, particularly charged particles, such as beams of electrons. Charged particles include ions, such as positively charged ions, e.g., protons, carbon or oxygen ions. In some cases, the charged particles can be heavier than an electron or have a different charge than an electron (e.g., a positron). The radiation can be applied in an amount sufficient to change the molecular structure and/or supramolecular structure of the biomass material.

Other materials, such as hydrocarbon-containing materials, e.g., hydrocarbons and coal can be processed in an analogous manner. When coal is utilized, it can be in solid form, e.g, pulverized coal, or it can be in liquefied form. Coal can be liqufed by a number of techniques, such as by the Bergius process, the SRC-I and SRC-II (Solvent Refined Coal) processes and the NUS Corporation hydrogenation process. When coal is utilized, it can be lignite, flame coal, gas flame coal, fat coal, forge coal, non-baking coal, anthracite coal or mixtures of any one or more of these types of coal.

For example, protons, helium nuclei, argon ions, silicon ions, neon ions, carbon ions, phosphorus ions, oxygen ions or nitrogen ions can be utilized to modify the structure of the biomass, e.g., breakdown the molecular weight or increase the molecular weight of the biomass. In some embodiments, heavier particles can induce higher amounts of chain scission in comparison to electrons or photons. In addition, in some instances, positively charged particles can induce higher amounts of chain scission than negatively charged particles due to their acidity.

The material resulting from irradiating the combination can be used in any suitable application, such as any of those described herein, e.g., for fuel, food, or as use in composite materials. For example, some of the methods described herein further include removing the inorganic material, and then contacting the resulting material with an enzyme and/or a mircroorganism for a time and under conditions sufficient to convert the carbohydrate-containing material to a fuel, such as ethanol or butanol (e.g., n-butanol). In other embodiments, the method further includes contacting the combination with an enzyme and/or a mircroorganism for a time and under conditions sufficient to convert the carbohydrate-containing material to a fuel, such as ethanol or butanol. In some embodiments, the methods include contacting the treated biomass material (with or without the inorganic material) with an enzyme to saccharify the material, and then inoculating the saccharified material with a microorganism to make a useful product, such as a fuel, such as ethanol, butanol or a hydrocarbon. If desired, the inorganic material can be separated and utilized again in the irradiating process.

In certain aspects, the invention features methods of making a carbohydrate-containing material that include combining a cellulosic and/or lignocellulosic material with an inorganic material, such as a metal or a metallic compound, a refractory material, a ceramic or mixtures of any of these, to provide a combination; and irradiating the combination. Irradiation may be, for example, with accelerated particles, such as electrons, e.g., at a speed of greater than seventy five percent of the speed of light.

In some implementations, the cellulosic or lignocellulosic materials can be selected from the group consisting of paper, paper products, wood, wood-related materials, such as sawdust and particle board, grasses, such as straw and switchgrass, rice hulls, bagasse, alfalfa, hay, cotton, jute, hemp, flax, bamboo, sisal, abaca; agricultural wastes, such as corn cobs, corn stover, bagasse and coconut hair; algae, seaweed, sewage, silage, synthetic celluloses, extruded yarn scrap textile materials, rags, and mixtures thereof.

The cellulosic and/or lignocellulosic and inorganic materials can be combined, for example, by dry blending or by co-comminuting the cellulosic and/or lignocellulosic material and inorganic materials together. Co-comminution can be performed while each material is cooled, e.g., to a temperature below 25° C., 0° C., the normal atmospheric sublimation temperature of dry ice, or even at or below the normal atmospheric boiling point of liquid nitrogen.

In certain embodiments, the inorganic material can be or include a metal or a metal alloy, e.g., a base metal, such as iron, nickel, lead, copper, or zinc, or a ferrous metal such as wrought iron or pig iron, or a noble metal, such as tantalum, gold, platinum, or rhodium. The metal or metal alloy can also be or include a precious metal, such as ruthenium, rhodium, palladium, osmium, iridium or platinum, or a transition metal. The metal alloy can be, e.g., steel, brass, bronze, duralumin, or hastaloy. The metal can be aluminum. In certain embodiments, the inorganic material can be or include a metallic compound, such as inorganic compound of iron or cobalt, and the inorganic compound can be in the 2+ or 3+ oxidation state.

In other embodiments, the inorganic material can be or include a refractory material, such as an acidic, neutral, or basic refractory material. The acid refractory material can be zircon, fireclay, or silica. The neutral refractory material can be alumina, chromite, silicon carbide, carbon, or mulitite. The basic refractory material can be or include dolomite or magnesite.

In some embodiments, the inorganic material can be or include a ceramic, such as an oxide, a carbide, a boride, a nitride, a silicide, or a kaolin, and the oxide can be or include an aluminum oxide, such as alumina, a zirconium oxide, a silicon oxide, a zinc oxide, or a titanium oxide, such as titanium dioxide.

In certain embodiments, the inorganic material includes water that is capable of leaving the inorganic material at elevated temperatures, such as hydrated alumina. In some embodiments, the inorganic material does not have a melting point. In other embodiments, the inorganic material has a melting point of greater than about 400° C., such as greater than about 500, 600, 700, 800, 900, 1000, 1200, 1,400, 1600, 1800, 2000, 2200, 2400, 2600 or even greater than about 2800° C.

The inorganic materials useful in the methods described herein can have a specific heat capacity Cp of less than about 1.5, such as less than about 1.25, 1.0, 0.75, 0.50, 0.25 or even less than about 0.1 J/gK. For example, the inorganic materials can have a specific heat capacity Cp of between about 1.25 and about 0.2 J/gK, such between about 1.15 and about 0.25 or between about 0.85 and 0.30 J/gK. In addition, the inorganic materials can have a conductivity of between about 0.004 and about 450 W/mK, between about 0.04 and about 250 W/mK, between about 0.1 and about 150 or between about 0.25 and about 50 W/mK, and a density of greater than about 1.5 g/cm$^3$, such as greater than about 2.0, 2.5. 3.0, 5.0, 7.0, 8.0, 9.0, 12.0, 15.0, 18.0, or even greater than 20.0 g/cm$^3$. In other embodiments, the inorganic material has a density of between about 3.5 g/cm$^3$ and about 20.0 g/cm$^3$, between about 4.0 g/cm$^3$ and about 18 g/cm$^3$ or between about 4.5 g/cm$^3$ and about 13 g/cm$^3$.

In certain embodiments, the inorganic materials can be in the form of particles that are substantially spherical in shape, and the average particle size can range from about 0.1 micron to about 100 microns, from about 0.25 micron to about 75 microns or from about 0.5 micron to about 50 microns.

The irradiating of the combination can include subjecting the combination to accelerated electrons, such as electrons having an energy of greater than about 2 MeV, 4 MeV, 6 MeV or even greater than about 8 MeV.

In some embodiments, the combination includes about 0.05 to about 35, about 0.1 to about 20, or about 0.5 to about 10 percent by weight inorganic material.

Some methods further include contacting the irradiated cellulosic and/or lignocellulosic material, with or without first removing the inorganic material, with an enzyme and/or a microorganism for a time and under conditions sufficient to convert the carbohydrate-containing material to a fuel, such as ethanol or butanol.

In another aspect, the invention features compositions of matter that include in combination, e.g., in homogeneous combination, a particulate carbohydrate-containing material and a particulate inorganic material, such as a metal or a metallic compound, a refractory material, a ceramic or mixtures of any of these.

Generally, the inorganic material is exogenous to the carbohydrate-containing material. The composition of matter can include, for example, at least about 0.5 percent by weight inorganic material, such as at least about 1, 3, 5, 10 or 25 percent by weight inorganic material, or between about 0.5 and about 25 percent by weight inorganic material, or between about 1 and about 15 percent by weight inorganic material.

The methods for making and processing materials from biomass can include functionalizing biomass. In some instances, functionalized biomass is more soluble and is more readily utilized by microorganisms in comparison to biomass that has not been functionalized. In addition, many of the functionalized materials described herein are less prone to oxidation and can have enhanced long-term stability (e.g., oxidation in air under ambient conditions).

In some implementations, the biomass feedstock is prepared by shearing a biomass fiber source to provide a fibrous material. For example, the shearing can be performed with a rotary knife cutter. The fibers of the fibrous material can have, e.g., an average length-to-diameter ratio of greater than 5/1. The fibrous material can have, e.g., a BET surface area of greater than 0.25 m$^2$/g. In some cases, the biomass can have a bulk density of less than about 0.35 g/cm$^3$. Low bulk density materials can be deeply penetrated by charged particles. For example, for electrons at an average energy of 5 MeV and a material with a bulk density of 0.35 g/cm$^3$, electron penetration depths can be 5-7 inches or more.

In another aspect, the invention features a method of processing a hydrocarbon-containing material, the method including irradiating a combination formed by combining a hydrocarbon-containing material with an inorganic material.

In some aspects, the hydrocarbon-containing material is selected from the group consisting of tar or oil sands, oil shale, crude oil, bitumen, coal, petroleum gases, liquefied natural and/or synthetic gas, and asphalt.

Combinations (e.g., blends) of hydrocarbon-containing materials, e.g., hydrocarbons and coal, and biomass can be processed in an analogous manner.

When a microorganism is utilized in the processes described herein, it can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures may be utilized. Generally, various microorganisms can produce a number of useful products, such as a fuel, by operating on, e.g., fermenting the materials. For example, fermentation or other processes can be used to produce alcohols, organic acids, hydrocarbons, hydrogen, proteins, or mixtures of any of these materials.

Examples of products that may be produced include mono- and polyfunctional C1-C6 alkyl alcohols, mono- and poly-functional carboxylic acids, C1-C6 hydrocarbons, and combinations thereof. Specific examples of suitable alcohols include methanol, ethanol, propanol, isopropanol, butanol, ethylene glycol, propylene glycol, 1,4-butane diol, glycerin, and combinations thereof. Specific example of suitable carboxylic acids include formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid, γ-hydroxybutyric acid, and combinations thereof. Examples of suitable hydrocarbons include methane, ethane, propane, pentane, n-hexane, and combinations thereof. Many of these products may be used as fuels.

Changing a molecular structure of a biomass feedstock, as used herein, means to change the chemical bonding arrangement, such as the type and quantity of functional groups or conformation of the structure. For example, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or an changing an overall domain size.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

This application incorporates by reference herein the entire contents of International Application No. PCT/US2007/022719, filed Oct. 26, 2007; applications to which the aforementioned claims priority; Ser. Nos. 61/049,391, 61/049,395, 61/049,419, 61/049,415, 61/049,413, 61/049,407, 61/049,404, 61/049,394, and 61/049,405, each filed on Apr. 30, 2008. This application also incorporates by reference in their entireties the disclosures of the U.S. patent applications having the following Ser. Nos. 12/486,436, 12/429,045, 12/417,904, 12/417,900, 12/417,880, 12/417,840, 12/417,786, 12/417,731, 12/417,723, 12/417,720, 12/417,707, 12/417,699, and 12/374,549.

The entire contents of each of the following publications are incorporated herein by reference: J. R. Adney et al., IEEE Transactions on Nuclear Science, Vol. NS-32, pp. 1841-1843 (1985); J. R. Adney et al., Proceedings of the 1989 IEEE Particle Accelerator Conference, Vol. 1, pp. 348-350 (1989); J. A. Ferry et al., Nuclear Instruments and Methods in Physics Research, Vol. B64, pp. 309-312 (1992); J. Ferry, in Handbook of Accelerator Physics and Engineering, pp. 16-17 (1999); J. A. Ferry et al., Nuclear Instruments and Methods in Physics Research A, Vol. 382, pp. 316-320 (1996); J. A. Ferry, Nuclear Instruments and Methods in Physics Research A, Vol. 328, pp. 28-33 (1993); T. M. Hauser et al., Nuclear Instruments and Methods in Physics Research B, Vol. 249, pp. 932-934 (2006); R. G. Herb, in Encyclopedia of Physics, pp. 3-8 (1981); R. G. Herb et al., in Encyclopedia of Applied Physics, Vol. 1, pp. 27-42 (1991); R. G. Herb, IEEE Transactions on Nuclear Science, Vol. NS-30, pp. 1359-1362 (1983); R. G. Herb, Proceedings of the Third International Conference on Electrostatic Accelerator Technology (1981); G. M. Klody et al., Nuclear Instruments and Methods in Physics Research B, Vol. 56-57, pp. 704-707 (1991); G. M. Klody et al., Nuclear Instruments and Methods in Physics Research B, Vol. 240, pp. 463-467 (2005); R. L. Loger, Application of Accelerators in Research and Industry, Proceedings of the Fifteenth International Conference, pp. 640-643 (1999); G. A. Norton et al., Nuclear Instruments and Methods in Physics Research B, Vol. 40-41, pp. 785-789 (1989); G. A. Norton et al., Application of Accelerators in Research and Industry, Proceedings of the Fourteenth International Conference, pp. 1109-1114 (1997); G. Norton et al., Handbook of Accelerator Physics and Engineering, pp. 24-26 (1999); G. A. Norton et al., Symposium of North Eastern Accelerator Personnel, pp. 295-301 (1992); G. Norton, Pramana, Vol. 59, pp. 745-751 (2002); G. A. Norton et al., Nuclear Instruments and Methods in Physics Research B, Vol. 37-38, pp. 403-407 (1989); G. A. Norton, Heavy Ion Accelerator Technology: Eighth International Conference, pp. 3-23 (1999); J. E. Raatz et al., Nuclear Instruments and Methods in Physics Research A, vol. 244, pp. 104-106 (1986); R. D. Rathmell et al., Nuclear Instruments and Methods in Physics Research B, vol. 56-57, pp. 1072-1075 (1991); J. B. Schroeder et al., Nuclear Instruments and Methods in Physics Research B, Vol. 56-57, pp. 1033-1035 (1991); J. B. Schroeder, Nuclear Instruments and Methods in Physics Research B, Vol. 40-41, pp. 535-537 (1989); J. B. Schroeder et al., Radiocarbon, Vol. 46 (2004); J. B. Schroeder et al., Nuclear Instruments and Methods in Physics Research B, Vol. 24-25, pp. 763-766 (1987); P. H. Stelson et al., Nuclear Instruments and Methods in Physics Research A, Vol. 244, pp. 73-74 (1986); M. L. Sundquist et al., Nuclear Instruments and Methods in Physics Research B, Vol. 99, pp. 684-687 (1995); M. L. Sundquist et al., Nuclear Instruments and Methods in Physics Research A, Vol. 287, pp. 87-89 (1990); and M. L. Sundquist, Applications of Accelerators in Research and Industry, Proceedings of the Fifteenth International Conference, pp. 661-664 (1999). All other patents, patent applications, and references cited herein are also incorporated by reference.

Other features and advantages of the invention will be apparent from the following detailed description, and from the claims.

DETAILED DESCRIPTION

Figure 1:
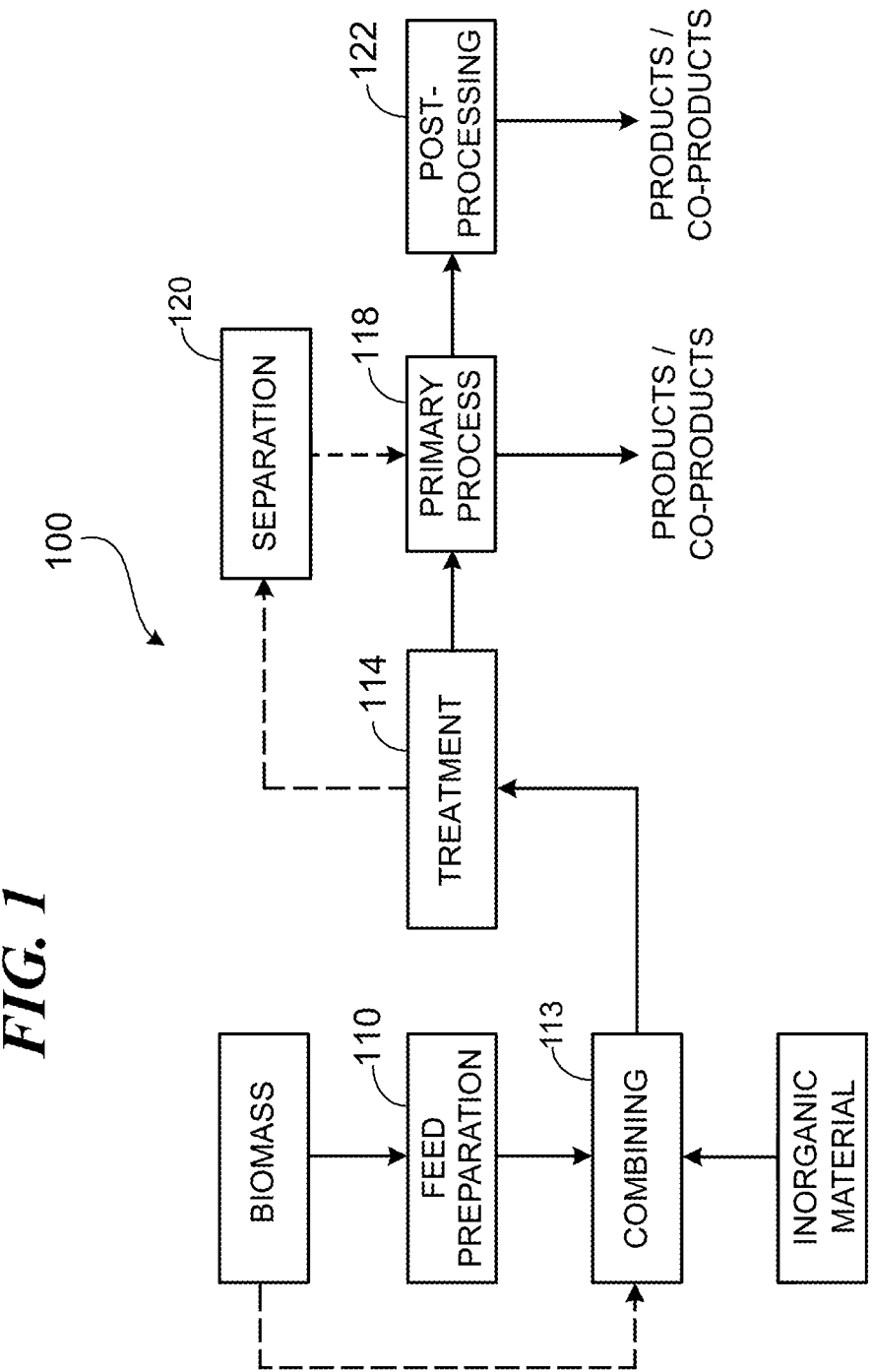
FIG. 1 is a block diagram illustrating conversion of biomass into products and co-products.

Systems and processes are described below that can use various biomass materials to form useful products. The biomass material is combined with one or more inorganic materials such as ceramics, metals, clays, and/or minerals and the combination is irradiated. The addition of the inorganic material modulates (increases/enhances or decreases) the effects of the radiation on the biomass in comparison to applying the same energy without the inorganic material being present. For example, the presence of the inorganic material can enhance the effect of the radiation on the biomass material by increasing the heat generated by irradiating.

For example, with the inorganic material present during irradiation, the degree of recalcitrance of the cellulosic or lignocellulosic material to structural change can be reduced to a greater extent for a given radiation dose relative to the case in which the inorganic material is not present during radiation treatment. For example, for any given dose, the average molecular weight and/or average crystallinity can be reduced by a greater degree, such as by 10, 20, 30, 40, 50, 60 or even 75 percent greater, when a combination of biomass and inorganic material is irradiated in comparison to a radiation treatment of biomass without the inorganic material being present during the irradiation. For example, for any given dose, the surface area and/or the porosity of the biomass can be increased by a greater degree, such as by 10, 20, 30, 40, 50, 60 or even 75 percent greater, when a combination of biomass and inorganic material is irradiated in comparison to the inorganic additive not being present during the irradiation.

Without wishing to be bound by any particular theory, it is believed that the inorganic additive can modulate the effects of the radiation on the biomass through a number of potential mechanisms, including thermal effects, activation effects (e.g., formation of reactive forms of the inorganic material), and secondary radiation effects (e.g., bremsstrahlung x-rays). Thermal effects are believed to arise from the heating of the biomass by the inorganic material that is heated in the radiation field when the kinetic energy of the particles is converted to heat. Molecular activation effects are believed to arise from the conversion of the inorganic material into a more chemically active species, which in turn reacts directly with the biomass or with a gas, such as air in the radiation field. For example, in an embodiment in which titanium dioxide is present in the inorganic material, the titanium dioxide can be activated in the radiation field to an electronically excited form of titanium dioxide, which in turn can react with oxygen in the air to generate ozone about the biomass. Ozone can attack the biomass, especially the lignin portions of the biomass.

With respect to thermal effects on inorganic materials in electron beams, differential electron beam absorption (dE/dx) in matter is described by equation (1):

$$dE/dx = -S(V)\rho \text{ (in MeV/cm)} \quad (1),$$

where $S(V)$ (MeV·cm$^2$/g) is the stopping power of the material to electrons at energy V, and $\rho$ is the mass density of the material (in g/cm$^3$).

Using the same parameters, the electron range (R), which is the maximum penetration distance of electrons of energy $V_0$ into the material, is approximated by equation (2):

$$R = V_0/S(V_0)\rho \text{ (in cm)} \quad (2).$$

Assuming no heat conduction, the temperature rise ($\Delta T$ in K) in a material being irradiated with energetic electrons is inversely proportion to the specific heat capacity of the material ($C_p$), material density ($\rho$), unit area (a) and thickness (d), and directly proportional to the deposited energy density ($\varepsilon$), as shown in equation (3):

$$\Delta T = \varepsilon/C_p \rho a d \text{(in K)} \quad (3).$$

When heat conduction is considered, heat is conducted away from the heated region and equilibrates on a time scale ($\tau$) that is inversely proportional the thermal conductivity of the material. If energy is put into the material on a time scale shorter than ($\tau$), the material will rise in temperature. With a beam of electrons it is possible to locally elevate temperatures of a material being irradiated up to 25,000° C. or greater.

Examples of suitable inorganic materials are discussed below in the MATERIALS section.

In some implementations, the biomass material is first physically prepared for processing, often by size reduction of a raw feedstock. In some cases, the biomass material and/or the combination is treated with one or more additional processing steps such as sonication, oxidation, pyrolysis, or steam explosion.

The irradiated combination of biomass and inorganic material can be used as a product in itself, or can be further processed to form one or more products and in some cases co-products, as will be discussed below. The inorganic material may be removed before, during or after further processing, or may remain in the final product(s).

Systems for Treating Biomass

FIG. 1 shows a system 100 for converting biomass, particularly biomass with significant cellulosic and lignocellulosic components and/or starchy components, into useful products and co-products. System 100 includes a feed preparation subsystem 110, a combining unit 113, a treatment subsystem 114, a primary process subsystem 118, and a post-processing subsystem 122. Feed preparation subsystem 110 receives biomass in its raw form, physically prepares the biomass for use as feedstock by downstream processes (e.g., reduces the size of and homogenizes the biomass), and stores the biomass both in its raw and feedstock forms. In the combining unit 113, the biomass is combined with an inorganic material, which is generally in particulate form.

Treatment subsystem 114 receives the combination from the combining unit 113, and prepares the feedstock for use in a primary production process such as fermentation by, for example, reducing the average molecular weight and crystallinity of the feedstock. In the treatment subsystem 114, the combination is irradiated, and may also be subjected to other treatments, such as quenching, pyrolysis, or oxidation.

Primary process subsystem 118 receives the treated feedstock from pretreatment subsystem 114 and uses it as a feedstock to produce useful products (e.g., ethanol, other alcohols, pharmaceuticals, and/or food products).

The feed preparation system, combining unit, treatment subsystem, and primary process subsystem 118 may be in the same production facility, or may be in two or more production facilities. For example, the biomass material can be physically prepared at a first facility, combined with the inorganic material and irradiated at a second facility, and processed in a primary process at the second facility or a third facility.

In some cases, the output of primary process subsystem 118 is directly useful but, in other cases, all or a portion of the output may require further processing, e.g., distillation, provided by post-processing subsystem 122. Post-processing subsystem 122 can also provide treatment for waste streams from the other subsystems. In some cases, the co-products of subsystems 114, 118, 122 can also be directly or indirectly useful as secondary products and/or in increasing the overall efficiency of system 100. For example, post-processing subsystem 122 can produce treated water to be recycled for use as process water in other subsystems and/or can produce burnable waste which can be used as fuel for boilers producing steam and/or electricity.

The inorganic material may in some cases be separated from the treated feedstock by a separation unit 120. Separation unit 120 may be before the primary process subsystem 118, as shown, or may be after the primary process subsystem or post-processing subsystem, or integrated with either of these subsystems. In some cases the inorganic material is recovered, e.g., to be re-used in the process or used as a co-product. In other cases the inorganic material is discarded. In some implementations the inorganic material is not separated from the biomass but instead becomes part of the final product.

Biomass Feedstock Preparation

In some cases, feed preparation system 110 prepares the feedstock by cutting, grinding, shearing, shredding, mechanical ripping or tearing, pin grinding, air attrition milling, or chopping. If desired, screens and/or magnets can be used to remove oversized or undesirable objects such as, for example, rocks or nails from the feed stream. Such physical preparation, e.g., by shearing, can be "open up" and stress the fibrous materials, making the cellulose of the materials more susceptible to chain scission and/or reduction of crystallinity. The open materials can also be more susceptible to oxidation when irradiated. Physical preparation can also make it easier to combine the biomass material with the inorganic material, for example by reducing the size of the biomass material and rendering it more homogeneous in size and shape.

Figure 2:
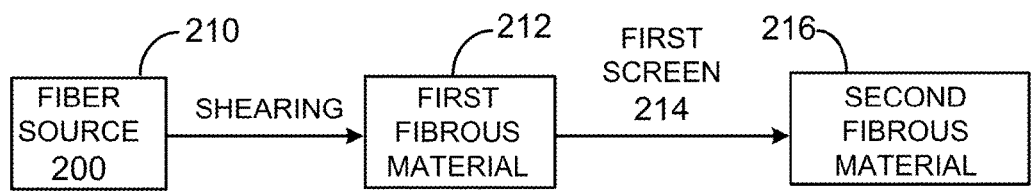
FIG. 2 is block diagram illustrating conversion of a fiber source into a first and second fibrous material.

In the example shown in FIG. 2, a biomass fiber source 210 is sheared, e.g., in a rotary knife cutter, to provide a first fibrous material 212. The first fibrous material 212 is passed through a first screen 214 having an average opening size of 1.59 mm or less (1/16 inch, 0.0625 inch) to provide a second fibrous material 216. If desired, the biomass fiber source can be cut prior to shearing, e.g., with a shredder, for example, a counter-rotating screw shredder, such as those manufactured by Munson (Utica, N.Y.), or with a guillotine cutter.

Figure 3:
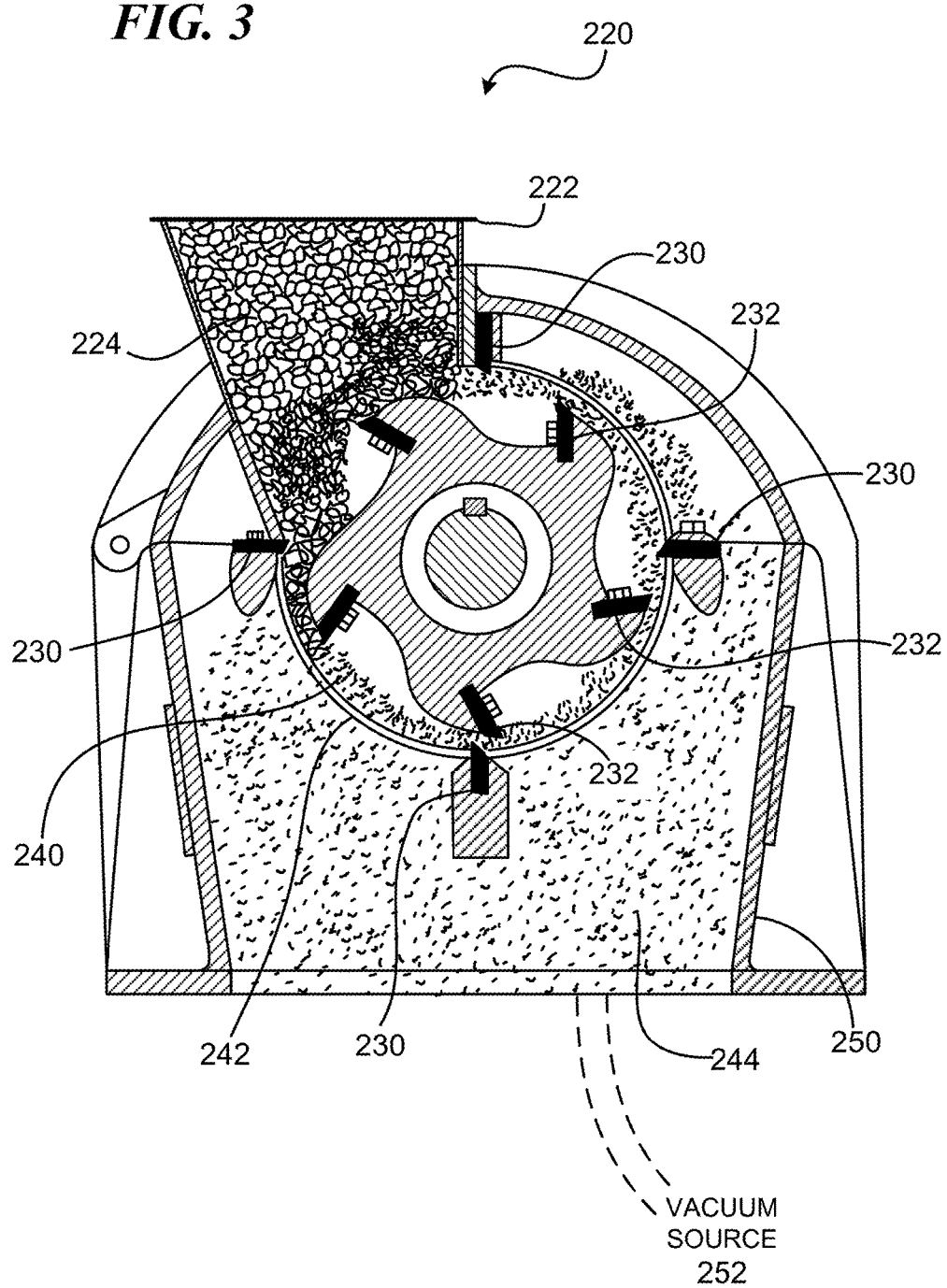
FIG. 3 is a cross-sectional view of a rotary knife cutter.

In some implementations, a rotary knife cutter is used to concurrently shear the fiber source and screen the first fibrous material. Referring to FIG. 3, a rotary knife cutter 220 includes a hopper 222 that can be loaded with a shredded fiber source 224 prepared by shredding fiber source. Shredded fiber source is sheared between stationary blades 230 and rotating blades 232 to provide a first fibrous material 240. First fibrous material 240 passes through screen 242, and the resulting second fibrous material 244 is captured in bin 250. To aid in the collection of the second fibrous material, the bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source 252 is utilized to maintain the bin below nominal atmospheric pressure. Suitable characteristics of the screen are described, for example, in U.S. Ser. No. 12/429,045.

The fiber source can be sheared in a dry state, a hydrated state (e.g., having up to ten percent by weight absorbed water), or in a wet state, e.g., having between about 10 percent and about 75 percent by weight water. The fiber source can even be sheared while partially or fully submerged under a liquid, such as water, ethanol, isopropanol. The fiber source can also be sheared in under a gas (such as a stream or atmosphere of gas other than air), e.g., oxygen or nitrogen, or steam.

If desired, the fibrous materials can be separated, e.g., continuously or in batches, into fractions according to their length, width, density, material type, or some combination of these attributes. For example, for forming composites, it is often desirable to have a relatively narrow distribution of fiber lengths.

The fibrous materials can irradiated immediately following their preparation, or they can may be dried, e.g., at approximately 105° C. for 4-18 hours, so that the moisture content is, e.g., less than about 0.5% before use.

Figure 4:
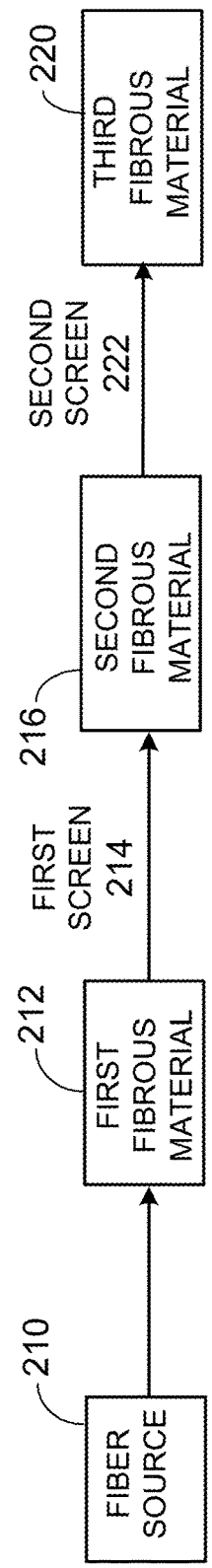
FIG. 4 is block diagram illustrating conversion of a fiber source into a first, second and third fibrous material.

In some embodiments, the second fibrous material is sheared and passed through the first screen, or a different sized screen. In some embodiments, the second fibrous material is passed through a second screen having an average opening size equal to or less than that of first screen. Referring to FIG. 4, a third fibrous material 220 can be prepared from the second fibrous material 216 by shearing the second fibrous material 216 and passing the resulting material through a second screen 222 having an average opening size less than the first screen 214. The sequence of shearing and screening can be repeated as many times as desired to obtain particular fiber properties.

Generally, the fibers of the fibrous materials can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (i.e., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

The average length-to-diameter ratio of the second fibrous material 14 can be, e.g., greater than 8/1, e.g., greater than 10/1, greater than 15/1, greater than 20/1, greater than 25/1, or greater than 50/1. An average length of the second fibrous material 14 can be, e.g., between about 0.5 mm and 2.5 mm, e.g., between about 0.75 mm and 1.0 mm, and an average width (i.e., diameter) of the second fibrous material 14 can be, e.g., between about 5 µm and 50 µm, e.g., between about 10 µm and 30 µm.

In some embodiments, a standard deviation of the length of the second fibrous material 14 is less than 60 percent of an average length of the second fibrous material 14, e.g., less than 50 percent of the average length, less than 40 percent of the average length, less than 25 percent of the average length, less than 10 percent of the average length, less than 5 percent of the average length, or even less than 1 percent of the average length.

In some embodiments, the material has a bulk density of less than 0.25 g/cm$^3$, e.g., 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

In some embodiments, a BET surface area of the second fibrous material is greater than 0.1 m$^2$/g, e.g., greater than 0.25 m$^2$/g, greater than 0.5 m$^2$/g, greater than 1.0 m$^2$/g, greater than 1.5 m$^2$/g, greater than 1.75 m$^2$/g, greater than 5.0 m$^2$/g, greater than 10 m$^2$/g, greater than 25 m$^2$/g, greater than 35 m$^2$/g, greater than 50 m$^2$/g, greater than 60 m$^2$/g, greater than 75 m$^2$/g, greater than 100 m$^2$/g, greater than 150 m$^2$/g, greater than 200 m$^2$/g, or even greater than 250 m$^2$/g. A porosity of the second fibrous material 14 can be, e.g., greater than 20 percent, greater than 25 percent, greater than 35 percent, greater than 50 percent, greater than 60 percent, greater than 70 percent, e.g., greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, a ratio of the average length-to-diameter ratio of the first fibrous material to the average length-to-diameter ratio of the second fibrous material is, e.g., less than 1.5, e.g., less than 1.4, less than 1.25, less than 1.1, less than 1.075, less than 1.05, less than 1.025, or even substantially equal to 1.

Any fibrous material described herein, or any mixture of fibrous material with an inorganic material, can be densified before or after irradiation, e.g., for transport or storage, and then "opened up" for further processing by any one or more methods described herein. Densification is described, for example, in U.S. Ser. No. 12/429,045.

Combination of the Biomass Material with the Inorganic Material

In some embodiments, the cellulosic and/or lignocellulosic material and inorganic material are combined by dry blending, such as in a drum prior to irradiating. In other embodiments, the cellulosic and/or lignocellulosic material and the inorganic material are co-comminuted. For example, the cellulosic and/or lignocellulosic material and inorganic material can be ground together in a mill prior to irradiation of the mixture. In particular embodiments, the cellulosic and/or lignocellulosic material and inorganic material are co-comminuted in a freezer mill such that each material is cooled to a temperature below 25° C., such as at or below 0° C., such as at or below the normal atmospheric sublimation temperature of dry ice, or at or below the normal atmospheric boiling point of liquid nitrogen. Grinding biomass in a freezer mill is described in U.S. Provisional Patent Application Ser. No. 61/081,709, entitled "Cooling and Processing Materials," which is incorporated herein by reference in its entirety.

Treatment

Treatment includes irradiating the combination of the physically prepared biomass material and the inorganic material. In some cases, treatment can further include one or more of sonication, oxidation, pyrolysis, and steam explosion, any of which can be modulated, e.g., enhanced, by the use of inorganic additives as described herein.

Radiation Treatment

Irradiating the combination can include subjecting the combination to accelerated electrons, such as electrons having an energy of greater than about 2 MeV, 4 MeV, 6 MeV, or even greater than about 8 MeV. Thus, ranges, such as ranges of 2.0 to 8.0 MeV and 4.0 to 6.0 MeV, are contemplated. In some embodiments, electrons are accelerated to, for example, a speed of greater than 75 percent of the speed of light, e.g., greater than 85, 90, 95, or 99 percent of the speed of light.

In some instances, the irradiation is performed at a dosage rate of greater than about 0.25 Mrad per second, e.g., greater than about 0.5, 0.75, 1.0, 1.5, 2.0, or even greater than about 2.5 Mrad per second. In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, the irradiating (with any radiation source or a combination of sources) is performed until the material receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad.

The dose applied will depend on the desired effect and the particular feedstock. For example, high doses of radiation can break chemical bonds within feedstock components and low doses of radiation can increase chemical bonding (e.g., cross-linking) within feedstock components.

Radiation can be applied to any sample that is dry or wet, or even dispersed in a liquid, such as water. For example, irradiation can be performed on cellulosic and/or lignocellulosic material in which less than about 25 percent by weight of the cellulosic and/or lignocellulosic material has surfaces wetted with a liquid, such as water. In some embodiments, irradiating is performed on cellulosic and/or lignocellulosic material in which substantially none of the cellulosic and/or lignocellulosic material is wetted with a liquid, such as water.

In some embodiments, any processing described herein occurs after the cellulosic and/or lignocellulosic material remains dry as acquired or has been dried, e.g., using heat and/or reduced pressure. For example, in some embodiments, the cellulosic and/or lignocellulosic material has less than about five percent by weight retained water, measured at 25° C. and at fifty percent relative humidity.

Radiation can be applied while the cellulosic and/or lignocellulosic is exposed to air, oxygen-enriched air, or even oxygen itself, or blanketed by an inert gas such as nitrogen, argon, or helium. When maximum oxidation is desired, an oxidizing environment is utilized, such as air or oxygen and the distance from the radiation source is optimized to maximize reactive gas formation, e.g., ozone and/or oxides of nitrogen.

Radiation may be applied under a pressure of greater than about 2.5 atmospheres, such as greater than 5, 10, 15, 20, or even greater than about 50 atmospheres.

Irradiating can be performed utilizing an ionizing radiation, such as gamma rays, x-rays, energetic ultraviolet radiation, such as ultraviolet C radiation having a wavelength of from about 100 nm to about 280 nm, a beam of particles, such as a beam of electrons, slow neutrons or alpha particles. In some embodiments, irradiating includes two or more radiation sources, such as gamma rays and a beam of electrons, which can be applied in either order or concurrently.

In some embodiments, energy deposited in a material that releases an electron from its atomic orbital is used to irradiate the materials. The radiation may be provided by 1) heavy charged particles, such as alpha particles or protons, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission.

In some embodiments, the irradiated biomass has a number average molecular weight ($M_{N2}$) that is lower than the number average molecular weight of the biomass prior to irradiation ($^T M_{N1}$) by more than about 10 percent, e.g., 15, 20, 25, 30, 35, 40, 50 percent, 60 percent, or even more than about 75 percent.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some instances, the irradiated biomass has cellulose that has as crystallinity ($^TC_2$) that is lower than the crystallinity ($^TC_1$) of the cellulose of the biomass prior to irradiation. For example, ($^TC_2$) can be lower than ($^TC_1$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the irradiated biomass can have a level of oxidation ($^TO_2$) that is higher than the level of oxidation ($^TO_1$) of the biomass prior to irradiation. A higher level of oxidation of the material can aid in its dispersability, swellability and/or solubility, further enhancing the materials susceptibility to chemical, enzymatic or biological attack. The irradiated biomass material can also have more hydroxyl groups, aldehyde groups, ketone groups, ester groups or carboxylic acid groups, which can increase its hydrophilicity.

Ionizing Radiation

Each form of radiation ionizes the biomass via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part, due to their acidic nature. When particles are utilized, the particles can have the mass of a resting electron, or greater, e.g., 500, 1000, 1500, or 2000 or more, e.g., 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear, or continuous wave. For example, cyclotron type accelerators are available from IBA, Belgium, such as the Rhodatron® system, while DC type accelerators are available from RDI, now IBA Industrial, such as the Dynamitron®. Exemplary ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy", Columbus-Ohio, ICRU-IAEA Meeting, 18-20 Mar. 2006, Iwata, Y. et al., "Alternating-Phase-Focused IH-DTL for Heavy-Ion Medical Accelerators", Proceedings of EPAC 2006, Edinburgh, Scotland, and Leitner, C. M. et al., "Status of the Superconducting ECR Ion Source Venus", Proceedings of EPAC 2000, Vienna, Austria.

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient (see "Ionization Radiation" in PCT/US2007/022719).

Electromagnetic radiation can be subclassified as gamma rays, x rays, ultraviolet rays, infrared rays, microwaves, or radiowaves, depending on wavelength.

Gamma radiation has the advantage of a significant penetration depth into a variety of material in the sample. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Electron Beam

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

In some embodiments, electrons used to treat biomass material can have average energies of 0.05 c or more (e.g., 0.10 c or more, 0.2 c or more, 0.3 c or more, 0.4 c or more, 0.5 c or more, 0.6 c or more, 0.7 c or more, 0.8 c or more, 0.9 c or more, 0.99 c or more, 0.9999 c or more), where c corresponds to the vacuum velocity of light.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. Effectiveness of depolymerization of the feedstock slurry depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Tradeoffs in considering electron energies include energy costs; here, a lower electron energy may be advantageous in encouraging depolymerization of certain feedstock slurry (see, for example, Bouchard, et al, Cellulose (2006) 13: 601-610).

It may be advantageous to provide a double-pass of electron beam irradiation in order to provide a more effective depolymerization process. For example, the feedstock transport device could direct the feedstock (in dry or slurry form) underneath and in a reverse direction to its initial transport direction. Double-pass systems can allow thicker feedstock slurries to be processed and can provide a more uniform depolymerization through the thickness of the feedstock slurry.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available.

Ion Particle Beams

Particles heavier than electrons can be utilized to irradiate carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phoshorus ions, oxygen ions or nitrogen ions can be utilized. In some embodiments, particles heavier than electrons can induce higher amounts of chain scission. In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

Ion beam treatment is discussed in detail in U.S. Ser. No. 12/417,699.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

Combinations of Radiation Treatments

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

Quenching and Controlled Functionalization of Biomass

After treatment with one or more ionizing radiations, such as photonic radiation (e.g., X-rays or gamma-rays), e-beam radiation or particles heavier than electrons that are positively or negatively charged (e.g., protons or carbon ions), any of the mixtures of carbohydrate-containing materials and inorganic materials described herein become ionized; that is, they include radicals at levels that are detectable with an electron spin resonance spectrometer. The current practical limit of detection of the radicals is about $10^{14}$ spins at room temperature. After ionization, any biomass material that has been ionized can be quenched to reduce the level of radicals in the ionized biomass, e.g., such that the radicals are no longer detectable with the electron spin resonance spectrometer. For example, the radicals can be quenched by the application of a sufficient pressure to the biomass and/or by utilizing a fluid in contact with the ionized biomass, such as a gas or liquid, that reacts with (quenches) the radicals. The use of a gas or liquid to at least aid in the quenching of the radicals also allows the operator to control functionalization of the ionized biomass with a desired amount and kind of functional groups, such as carboxylic acid groups, enol groups, aldehyde groups, nitro groups, nitrile groups, amino groups, alkyl amino groups, alkyl groups, chloroalkyl groups or chlorofluoroalkyl groups. In some instances, such quenching can improve the stability of some of the ionized biomass materials. For example, quenching can improve the resistance of the biomass to oxidation. Functionalization by quenching can also improve the solubility of any biomass described herein, can improve its thermal stability, which can be important in the manufacture of composites, and can improve material utilization by various microorganisms. For example, the functional groups imparted to the biomass material by quenching can act as receptor sites for attachment by microorganisms, e.g., to enhance cellulose hydrolysis by various microorganisms.

If the ionized biomass remains in the atmosphere, it will be oxidized, such as to an extent that carboxylic acid groups are generated by reaction with the atmospheric oxygen. In some instances with some materials, such oxidation is desired because it can aid in the further breakdown in molecular weight of the carbohydrate-containing biomass, and the oxidation groups, e.g., carboxylic acid groups can be helpful for solubility and microorganism utilization in some instances. However, since the radicals can "live" for some time after irradiation, e.g., longer than 1 day, 5 days, 30 days, 3 months, 6 months or even longer than 1 year, material properties can continue to change over time, which in some instances, can be undesirable.

Detecting radicals in irradiated samples by electron spin resonance spectroscopy and radical lifetimes in such samples is discussed in Bartolotta et al., Physics in Medicine and Biology, 46 (2001), 461-471 and in Bartolotta et al., Radiation Protection Dosimetry, Vol. 84, Nos. 1-4, pp. 293-296 (1999), the contents of each of which are incorporated herein by reference.

Sonication, Pyrolysis, Oxidation

One or more sonication, pyrolysis, and/or oxidative processing sequences can be used to process raw feedstock from a wide variety of different sources to extract useful substances from the feedstock, and to provide partially degraded organic material which functions as input to further processing steps and/or sequences. Such processing can reduce the molecular weight and/or crystallinity of feedstock and biomass, e.g., one or more carbohydrate sources, such as cellulosic or lignocellulosic materials, or starchy materials. These processes are described in detail in U.S. Ser. No. 12/429,045.

Other Processes

Steam explosion can be used alone without any of the processes described herein, or in combination with any of the processes described herein.

Any processing technique described herein can be used at pressure above or below normal, earth-bound atmospheric pressure. For example, any process that utilizes radiation, sonication, oxidation, pyrolysis, steam explosion, or combinations of any of these processes to provide materials that include a carbohydrate can be performed under high pressure, which can increase reaction rates. For example, any process or combination of processes can be performed at a pressure greater than about greater than 25 MPa, e.g., greater than 50 MPa, 75 MPa, 100 MPa, 150 MPa, 200 MPa, 250 MPa, 350 MPa, 500 MPa, 750 MPa, 1,000 MPa, or greater than 1,500 MPa.

Primary Processes and Post-Processing

Materials treated using any of the processes described herein can then be subjected to other processes, for example primary processes such as fermentation and gasification, and/or post-processing steps such as distillation, wastewater processing, waste combustion, and the like. Such processes are described in detail in the patent applications that have been incorporated by reference herein, e.g., in Ser. No. 12/429,045.

Products/Co-Products

Using such primary processes and/or post-processing, the treated biomass can be converted to one or more products, for example alcohols, e.g., methanol, ethanol, propanol, isopropanol, butanol, e.g., n-, sec- or t-butanol, ethylene glycol, propylene glycol, 1, 4-butane diol, glycerin or mixtures of these alcohols; organic acids, such as formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, γ-hydroxybutyric acid or mixtures of these acids; food products; animal feed; pharmaceuticals; or nutriceuticals. Co-products that may be produced include lignin residue.

Materials

Inorganic Materials

In some embodiments, the inorganic material is or includes a metal or a metal alloy. For example, the metal can include a base metal, such as iron, nickel, lead, copper or zinc, a ferrous metal, such as wrought iron or pig iron, a noble metal, such as tantalum, gold, platinum or rhodium, a precious metal, such as ruthenium, rhodium, palladium, osmium, iridium, or platinum, or a transition metal, e.g., elements 21 to 30 (inclusive), 39 to 48 (inclusive), 71 to 80 (inclusive), and 103 to 112 from the periodic table of elements.

In specific embodiments, the inorganic material is or includes a metal alloy, such a binary or ternary alloy. In particular embodiments, the alloy is or includes steel, brass, bronze, duralumin, hastaloy, Al—Li alloy, alnico alloy, nambe alloy, silumin alloy, AA-8000 and magnalium alloy.

In one embodiment, the inorganic material is or includes aluminum, such as waste packaging that includes an aluminum layer.

In other embodiments, the inorganic material is or includes a metallic compound, such as inorganic compound of iron or cobalt, such as an inorganic iron or cobalt compound in which the iron or cobalt is in the 2+ or 3+ oxidation state. Examples of such iron compounds are ammonium iron(II) sulfate hexahydrate, ammonium iron(II) sulfate solution, ammonium iron(III) sulfate dodecahydrate, ammonium iron(III) sulfate, iron(II) sulfate heptahydrate, iron(II) sulfate hydrate, iron(II) sulfate solution, and iron (III) sulfate hydrate.

In still other embodiments, inorganic material is or includes a refractory material, such as an acidic, neutral or basic refractory. Examples of acidic refractory materials include zircon, fireclay and silica. Examples of neutral refractory materials include alumina, chromite, silicon carbide, carbon and mulitite. Examples of basic refractory materials include dolomite or magnesite.

In yet other embodiments, the inorganic material includes a ceramic, such as an oxide, a carbide, a boride, a nitride, a silicide, or a kaolin (e.g., natural, neutral, acidic, basic, or whitened). For example, the oxide can be an aluminum oxide, such as alumina, a zirconium oxide, a silicon oxide, a zinc oxide, or a titanium oxide, such as titanium dioxide.

In some embodiments, the inorganic additive includes between about 0.25 and about 25 percent by weight water therein and/or thereon. In a specific embodiment, the inorganic material includes water of hydration that is capable of leaving the inorganic material at elevated temperatures, such as hydrated alumina.

Other examples of useful inorganic materials include calcium carbonate, aragonite clay, orthorhombic clays, calcite clay, rhombohedral clays, bentonite clay, dicalcium phosphate, dicalcium phosphate anhydrous, dicalcium phosphate dihydrate, tricalcium phosphate, calcium pyrophosphate, insoluble sodium metaphosphate, precipitated calcium carbonate, magnesium orthophosphate, trimagnesium phosphate, hydroxyapatites, synthetic apatites, hydrated silica xerogel, metal aluminosilicate complexes, sodium aluminum silicates, zirconium silicate, sand, glass, stone, rock, montmorillonite, and shale.

In some embodiments, the inorganic material has a melting point of greater than about 400° C., such as greater than about 500, 600, 700, 800, 900, 1000, 1200, 1,400, 1600, 1800, 2000, 2200, 2400, 2600 or even greater than 2800° C. In other instances, the inorganic material does not have or does not include a material having a melting point.

In some instances, the inorganic material has a specific heat capacity $C_p$ of less than about 1.5 J/gK, such as less than about 1.25, 1.0, 0.75, 0.50, 0.25 or even less than about 0.1 J/gK. In various examples, the inorganic material can have a specific heat capacity $C_p$ of between about 1.25 and about 0.2 J/gK, such between about 1.15 and about 0.25 or between about 0.85 and 0.30 J/gK.

The inorganic material can have a thermal conductivity of between about 0.004 and about 450 W/mK, between about 0.04 and about 250 W/mK, between about 0.1 and about 150 W/mK, or between about 0.25 and about 50 W/mK.

The inorganic material can have a density of greater than about 1.5 g/cm$^3$, such as greater than about 2.0, 2.5, 3.0, 5.0, 7.0, 8.0, 9.0, 12.0, 15.0, 18.0, or even greater than 20.0 g/cm$^3$. The inorganic material can have a density of between about greater 3.5 g/cm³ and about 20.0 g/cm³, between about 4.0 g/cm³ and about 18 g/cm³ or between about 4.5 g/cm³ and about 13 g/cm³.

In some instances, the inorganic material is or includes particles which are substantially spherical in shape, and that have an average particle size, e.g., diameter, that ranges from about 0.1 micron to about 100 microns, from about 0.25 micron to about 75 microns or from about 0.5 micron to about 50 microns. In some cases, the particle size can range from about 10 mm to about 1000 mm. The particles may also be in the form of fibers, plates, or have other morphologies. The particles may have a surface area of, for example, about 0.5 to 500 m²/g.

To maximize the effect of the inorganic additive, the combination can have between about 0.05 to about 35 percent by weight inorganic material, such as between about 0.1 to about 20 percent by weight inorganic material or between about 0.5 and about 10 percent by weight of the inorganic material.

Biomass Materials

Generally, any biomass material that is or includes a carbohydrate, composed entirely of one or more saccharide units or that include one or more saccharide units, can be processed by any of the methods described herein. For example, the biomass material can be cellulosic, lignocellulosic, starch, or sugars.

For example, such materials can include fibrous materials such as paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these.

In some cases the biomass is a microbial material. Microbial sources include, but are not limited to, any naturally occurring or genetically modified microorganism or organism that contains or is capable of providing a source of carbohydrates (e.g., cellulose), for example, protists (e.g., animal (e.g., protozoa such as flagellates, amoeboids, ciliates, and sporozoa) and plant (e.g., algae such alveolates, chlorarachniophytes, cryptomonads, euglenids, glaucophytes, haptophytes, red algae, stramenopiles, and viridaeplantae)), seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Other biomass materials are discussed in the U.S. patent applications incorporated by reference hereinabove.

Other Embodiments

Low Dose Irradiation and Composites

While irradiation has been discussed above primarily in the context of reducing molecular weight and crystallinity of the biomass, in some embodiments, relatively low doses of radiation can crosslink, graft, or otherwise increase the molecular weight of a carbohydrate-containing material. Such a material having increased molecular weight can be useful, e.g., in making a composite having improved mechanical properties, such as abrasion resistance, compression strength, fracture resistance, impact strength, bending strength, tensile modulus, flexural modulus and elongation at break. Such a material having increased molecular weight can be useful in making a composition. Forming composites is described in WO 2006/102543, and in U.S. Ser. Nos. 12/417,720 and 12/429,045.

Alternatively, a material, e.g., a fibrous material that includes a first cellulosic and/or lignocellulosic material having a first molecular weight, in a mixture with an inorganic material, can be combined with a resin to provide a composite, and then the composite can be irradiated with a relatively low dose of radiation so as to provide a second cellulosic and/or lignocellulosic material having a second molecular weight higher than the first molecular weight. For example, if gamma radiation is utilized as the radiation source, a dose of from about 1 Mrad to about 10 Mrad can be applied. Using this approach increases the molecular weight of the material while it is within a resin matrix. In some embodiments, the resin is a cross-linkable resin and as such it crosslinks as the carbohydrate-containing material increases in molecular weight, which can provide a synergistic effect to provide advantageous mechanical properties to the composite.

Treatment of Hydrocarbon-Containing Materials

In some embodiments, the methods and systems disclosed herein can be used to process hydrocarbon-containing materials such as tar or oil sands, oil shale, crude oil (e.g., heavy crude oil and/or light crude oil), bitumen, coal, e.g., peat, lignite, sub-bituminous, bituminous and anthracite coal, petroleum gases (e.g., methane, ethane, propane, butane, isobutane), liquefied natural and/or synthetic gas, asphalt, and other natural materials that include various types of hydrocarbons. For example, a processing facility for hydrocarbon-containing materials receives a supply of raw material. The raw material can be delivered directly from a mine, e.g., by conveyor belt and/or rail car system, and in certain embodiments, the processing facility can be constructed in relatively close proximity to, or even atop, the mine. In some embodiments, the raw material can be transported to the processing facility via railway freight car or another motorized transport system, and/or pumped to the processing facility via pipeline.

When the raw material enters the processing facility, the raw material can be broken down mechanically and/or chemically to yield starting material. As an example, the raw material can include material derived from oil sands and containing crude bitumen. Bitumen can then be processed into one or more hydrocarbon products using the methods disclosed herein, for example by mixing the bitumen with an inorganic material as described herein and irradiating the mixture. In some embodiments, the oil sands material can be extracted from surface mines such as open pit mines. In certain embodiments, sub-surface oil sands material can be extracted using a hot water flotation process that removes oil from sand particles, and then adding naphtha to allow pumping of the oil to the processing facility.

For example, to process bitumen from oil sands, one or more of the techniques disclosed herein can be used prior to any mechanical breakdown steps, following one or more mechanical breakdown steps, prior to cracking, after cracking and/or prior to hydrotreatment, and after hydrotreatment. As another example, to process oil shale, one or more of the techniques disclosed herein can be used prior to either or both of the vaporization and purification steps discussed above. Products derived from the hydrocarbon-based raw materials can be treated again with any combination of techniques prior to transporting the products out of the processing facility (e.g., either via motorized transport, or via pipeline).

The techniques disclosed herein can be applied to process raw and/or intermediate material in dry form, in a solution or slurry, or in gaseous form (e.g., to process hydrocarbon vapors at elevated temperature). The solubility of raw or intermediate products in solutions and slurries can be controlled through selective addition of one or more agents such as acids, bases, oxidizing agents, reducing agents, and salts. In general, the methods disclosed herein can be used to initiate and/or sustain the reaction of raw and/or intermediate hydrocarbon-containing materials, extraction of intermediate materials from raw materials (e.g., extraction of hydrocarbon components from other solid or liquid components), distribution of raw and/or intermediate materials, and separation of intermediate materials from raw materials (e.g., separation of hydrocarbon-containing components from other solid matrix components to increase the concentration and/or purity and/or homogeneity of the hydrocarbon components).

In addition, microorganisms can be used for processing raw or intermediate materials, either prior to or following irradiation. Suitable microorganisms include various types of bacteria, yeasts, and mixtures thereof, as disclosed previously. The processing facility can be equipped to remove harmful byproducts that result from the processing of raw or intermediate materials, including gaseous products that are harmful to human operators, and chemical byproducts that are harmful to humans and/or various microorganisms.

In some embodiments, the use of one or more of the techniques disclosed herein results in a molecular weight reduction of one or more components of the raw or intermediate material that is processed. As a result, various lower weight hydrocarbon substances can be produced from one or more higher weight hydrocarbon substances. In certain embodiments, the use of one or more of the techniques disclosed herein results in an increase in molecular weight of one or more components of the raw or intermediate material that is processed. For example, the various techniques disclosed herein can induce bond-formation between molecules of the components, leading to the formation of increased quantities of certain products, and even to new, larger weight products. In addition to hydrocarbon products, various other compounds can be extracted from the raw materials, including nitrogen based compounds (e.g., ammonia), sulfur-based compounds, and silicates and other silicon-based compounds. In certain embodiments, one or more products extracted from the raw materials can be combusted to generate process heat for heating water, raw or intermediate materials, generating electrical power, or for other applications.

In some embodiments, processing raw and/or intermediate materials by mixing with an inorganic material and irradiating the mixture can lead to improvements in the efficiency (and even the elimination) of other processing steps. For example, processing oil sand materials (including bitumen) using one or more of the techniques disclosed herein can lead to more efficient cracking and/or hydrotreatment of the bitumen. As another example, processing oil shale can lead to more efficient extraction of various products, including shale oil and/or shale gas, from the oil shale. In certain embodiments, steps such as cracking or vaporization may not even be necessary if the techniques disclosed herein are first used to treat the raw material. Further, in some embodiments, by treating raw and/or intermediate materials, the products can be made more soluble in certain solvents, in preparation for subsequent processing steps in solution (e.g., steam blasting, sonication). Improving the solubility of the products can improve the efficiency of subsequent solution-based treatment steps. By improving the efficiency of other processing steps (e.g., cracking and/or hydrotreatment of bitumen, vaporization of oil shale), the overall energy consumed in processing the raw materials can be reduced, making extraction and processing of the raw materials economically feasible.

In certain embodiments, ion beams can be particularly efficient at processing raw hydrocarbon-containing materials. For example, due to the ability of ion beams to initiate both polymerization and depolymerization reactions, to deposit heat in the irradiated material, and to sputter or otherwise displace atoms of the irradiated material, hydrocarbon materials such as oil sands, oil shale, crude oil, asphalt, and other materials can be treated to improve additional processing steps for these materials and/or to extract useful products from the materials.

Products derived from processing hydrocarbon-containing materials can include one or more compounds suitable for use as fuels. The fuel compounds can be used on-site (e.g., combusted to generate electrical power) and/or can be transported to another facility for storage and/or use.

Processing of Crude Oil

The methods and systems disclosed herein can be used to process crude oil in addition to, or as an alternative to, conventional oil refining technologies. In particular, ion beam treatment methods—alone or in combination with any of the other methods disclosed herein—can be used for low temperature oil cracking, reforming, functionalization, and other processes.

Generally, treatment of crude oil and/or components thereof using the methods disclosed herein (including, for example, ion beam treatment, alone or in combination with one or more other methods) can be used to modify molecular weights, chemical structures, viscosities, solubilities, densities, vapor pressures, and other physical properties of the treated materials. Typical ions that can be used for treatment of crude oil and/or components thereof can include protons, carbon ions, oxygen ions, and any of the other types of ions disclosed herein. In addition, ions used to treat crude oil and/or its components can include metal ions; in particular, ions of metals that catalyze certain refinery processes (e.g., catalytic cracking) can be used to treat crude oil and/or components thereof. Exemplary metal ions include, but are not limited to, platinum ions, palladium ions, iridium ions, rhodium ions, ruthenium ions, aluminum ions, rhenium ions, tungsten ions, and osmium ions.

In some embodiments, multiple ion exposure steps can be used. A first ion exposure can be used to treat crude oil (or components thereof) to effect a first change in one or more of molecular weight, chemical structure, viscosity, density, vapor pressure, solubility, and other properties. Then, one or more additional ion exposures can be used to effect additional changes in properties. As an example, the first ion exposure can be used to convert a substantial fraction of one or more high boiling, heavy components to lower molecular weight compounds with lower boiling points. Then, one or more additional ion exposures can be used to cause precipitation of the remaining amounts of the heavy components from the component mixture.

In general, a large number of different processing protocols can be implemented, according to the composition and physical properties of the feedstock. In certain embodiments, the multiple ion exposures can include exposures to only one type of ion. In some embodiments, the multiple ion exposures can include exposures to more than one type of ion. The ions can have the same charges, or different charge magnitudes and/or signs.

In some embodiments, the crude oil and/or components thereof can be functionalized during exposure to ion beams. For example, the composition of one or more ion beams can be selected to encourage the addition of particular functional groups to certain components (or all components) of a crude oil feedstock. One or more functionalizing agents (e.g., ammonia) can be added to the feedstock to introduce particular functional groups. By functionalizing the crude oil and/or components thereof, ionic mobility within the functionalized compounds can be increased (leading to greater effective ionic penetration during exposure), and physical properties such as viscosity, density, and solubility of the crude oil and/or components thereof can be altered. By altering one or more physical properties of the crude oil and/or crude oil components, the efficiency and selectivity of subsequent refining steps can be adjusted, and the available product streams can be controlled. Moreover, functionalization of crude oil and/or crude oil components can lead to improved activating efficiency of catalysts used in subsequent refining steps.

In general, the methods disclosed herein—including ion beam exposure of crude oil and crude oil components—can be performed before, during, or after any of the other refining steps disclosed herein, and/or before, during, or after any other steps that are used to refine crude oil. The methods disclosed herein can also be used after refining is complete, and/or before refining begins. In certain embodiments, the methods disclosed herein, including ion beam exposure, can be used to process crude oil even during extraction of the crude oil from oil fields.

In some embodiments, when crude oil and/or components thereof are exposed to one or more ion beams, the exposed material can also be exposed to one or more gases concurrent with ion beam exposure. Certain components of crude oil, such as components that include aromatic rings, may be relatively more stable to ion beam exposure than non-aromatic components. Typically, for example, ion beam exposure leads to the formation of reactive intermediates such as radicals from hydrocarbons. The hydrocarbons can then react with other less reactive hydrocarbons. To reduce the average molecular weight of the exposed material, reactions between the reactive products and less reactive hydrocarbons lead to molecular bond-breaking events, producing lower weight fragments from longer chain molecules. However, more stable reactive intermediates (e.g., aromatic hydrocarbon intermediates) may not react with other hydrocarbons, and can even undergo polymerization, leading to the formation of heavier weight compounds. To reduce the extent of polymerization in ion beam exposed crude oil and/or crude oil components, one or more radical quenchers can be introduced during ion beam exposure. The radical quenchers can cap reactive intermediates, preventing the re-formation of chemical bonds that have been broken by the incident ions. Suitable radical quenchers include hydrogen donors such as hydrogen gas.

In certain embodiments, reactive compounds can be introduced during ion beam exposure to further promote degradation of crude oil and/or crude oil components. The reactive compounds can assist various degradation (e.g., bond-breaking) reactions, leading to a reduction in molecular weight of the exposed material. An exemplary reactive compound is ozone, which can be introduced directly as a gas, or generated in situ via application of a high voltage to an oxygen-containing supply gas (e.g., oxygen gas, air) or exposure of the oxygen-containing supply gas to an ion beam and/or an electron beam. In some embodiments, ion beam exposure of crude oil and/or crude oil components in the presence of a fluid such as oxygen gas or air can lead to the formation of ozone gas, which also assists the degradation of the exposed material.

Prior to and/or following distillation in a refinery, crude oil and/or components thereof can undergo a variety of other refinery processes to purify components and/or convert components into other products, for example catalytic cracking, alkylation, catalytic reforming and isomerization, and catalytic hydrocracking. The methods described herein can be integrated with such refinery processes if desired.

For example, the methods disclosed herein can be used before, during, and/or after catalytic cracking to treat components of crude oil. In particular, ion beam exposure (alone, or in combination with other methods) can be used to pre-treat feedstock prior to injection into the riser, to treat hydrocarbons (including hydrocarbon vapors) during cracking, and/or to treat the products of the catalytic cracking process.

Cracking catalysts typically include materials such as acid-treated natural aluminosilicates, amorphous synthetic silica-alumina combinations, and crystalline synthetic silica-alumina catalysts (e.g., zeolites). During the catalytic cracking process, components of crude oil can be exposed to ions from one or more ion beams to increase the efficiency of these catalysts. For example, the crude oil components can be exposed to one or more different types of metal ions that improve catalyst activity by participating in catalytic reactions. Alternatively, or in addition, the crude oil components can be exposed to ions that scavenge typical catalyst poisons such as nitrogen compounds, iron, nickel, vanadium, and copper, to ensure that catalyst efficiency remains high. Moreover, the ions can react with coke that forms on catalyst surfaces to remove the coke (e.g., by processes such as sputtering, and/or via chemical reactions), either during cracking or catalyst regeneration.

The methods disclosed herein can be used before, during, and/or after alkylation to treat components of crude oil. In particular, ion beam exposure (alone, or in combination with other methods) during alkylation can assist the addition reaction between olefins and isoparaffins. In some embodiments, ion beam exposure of the crude oil components can reduce or even eliminate the need for sulfuric acid and/or hydrofluoric acid catalysts, reducing the cost and the hazardous nature of the alkylation process. The types of ions, the number of ion beam exposures, the exposure duration, and the ion beam current can be adjusted to preferentially encourage 1+1 addition reactions between the olefins and isoparaffins, and to discourage extended polymerization reactions from occurring.

In catalytic reforming processes, hydrocarbon molecular structures are rearranged to form higher-octane aromatics for the production of gasoline; a relatively minor amount of cracking occurs. During reforming, the major reactions that lead to the formation of aromatics are dehydrogenation of naphthenes and dehydrocyclization of paraffins. The methods disclosed herein can be used before, during, and/or after catalytic reformation to treat components of crude oil. In particular, ion beam exposure (alone, or in combination with other methods) can be used to initiate and sustain dehydrogenation reactions of naphthenes and/or dehydrocyclization reactions of paraffins to form aromatic hydrocarbons. Single or multiple exposures of the crude oil components to one or more different types of ions can be used to improve the yield of catalytic reforming processes. For example, in certain embodiments, dehydrogenation reactions and/or dehydrocyclization reactions proceed via an initial hydrogen abstraction. Exposure to negatively charged, basic ions can increase the rate at which such abstractions occur, promoting more efficient dehydrogenation reactions and/or dehydrocyclization reactions. In some embodiments, isomerization reactions can proceed effectively in acidic environments, and exposure to positively charged, acidic ions (e.g., protons) can increase the rate of isomerization reactions.

Catalysts used in catalytic reformation generally include platinum supported on an alumina base. Rhenium can be combined with platinum to form more stable catalysts that permit lower pressure operation of the reformation process. Without wishing to be bound by theory, it is believed that platinum serves as a catalytic site for hydrogenation and dehydrogenation reactions, and chlorinated alumina provides an acid site for isomerization, cyclization, and hydrocracking reactions. In general, catalyst activity is reduced by coke deposition and/or chloride loss from the alumina support. Restoration of catalyst activity can occur via high temperature oxidation of the deposited coke, followed by chlorination of the support.

In some embodiments, ion beam exposure can improve the efficiency of catalytic reformation processes by treating catalyst materials during and/or after reformation reactions occur. For example, catalyst particles can be exposed to ions that react with and oxidize deposited coke on catalyst surfaces, removing the coke and maintaining/returning the catalyst in/to an active state. The ions can also react directly with undeposited coke in the reformation reactor, preventing deposition on the catalyst particles. Moreover, the alumina support can be exposed to suitably chosen ions (e.g., chlorine ions) to re-chlorinate the surface of the support. By maintaining the catalyst in an active state for longer periods and/or scavenging reformation by-products, ion beam exposure can lead to improved throughput and/or reduced operating costs of catalytic reformation processes.

The methods disclosed herein can be used before, during, and/or after catalytic hydrocracking to treat components of crude oil. In particular, ion beam exposure (alone, or in combination with other methods) can be used to initiate hydrogenation and/or cracking processes. Single or multiple exposures of the crude oil components to one or more different types of ions can be used to improve the yield of hydrocracking by tailoring the specific exposure conditions to various process steps. For example, in some embodiments, the crude oil components can be exposed to hydride ions to assist the hydrogenation process. Cracking processes can be promoted by exposing the components to reactive ions such as protons and/or carbon ions.

In certain embodiments, ion beam exposure can improve the efficiency of hydrocracking processes by treating catalyst materials during and/or after cracking occurs. For example, catalyst particles can be exposed to ions that react with and oxidize deposits on catalyst surfaces, removing the deposits and maintaining/returning the catalyst in/to an active state. The crude oil components can also be exposed to ions that correspond to some or all of the metals used for hydrocracking, including platinum, palladium, tungsten, and nickel. This exposure to catalytic ions can increase the overall rate of the hydrocracking process.

A variety of other processes that occur during the course of crude oil refining can also be improved by, or supplanted by, the methods disclosed herein. For example, the methods disclosed herein, including ion beam treatment of crude oil components, can be used before, during, and/or after refinery processes such as coking, thermal treatments (including thermal cracking), hydroprocessing, and polymerization to improve the efficiency and overall yields, and reduce the waste generated from such processes.

Other embodiments are within the scope of the following claims.

What is claimed is:

1. A method of processing a hydrocarbon-containing material, the method comprising: irradiating, with an ion beam comprising accelerated charged particles having energies of from 1 to 6000 MeV/atomic unit, a combination formed by combining the hydrocarbon-containing material with an inorganic material, to produce an irradiated combination, wherein the hydrocarbon-containing material is coal and the inorganic material comprises a ceramic.

2. The method of claim 1 wherein the hydrocarbon-containing material comprises a solid, particulate, powder, liquid, gas or a combination thereof.

3. The method of claim 1, wherein the hydrocarbon-containing material is combined with the inorganic material by dry blending or co-comminuting.

4. The method of claim 3, wherein during co-comminuting, each of the hydrocarbon-containing material and the inorganic material is cooled to a temperature below 25° C.

5. The method of claim 3, wherein during co-comminuting, each of the hydrocarbon-containing material and the inorganic material is cooled to a temperature below 0° C.

6. The method of claim 1, wherein the ceramic is selected from the group consisting of oxides, carbides, borides, nitrides, silicides and kaolins.

7. The method of claim 1, wherein the inorganic material comprises water that is capable of leaving the inorganic material at elevated temperatures.

8. The method of claim 1, wherein the inorganic material does not have a melting point.

9. The method of claim 1, wherein the inorganic material has a melting point of greater than about 400° C.

10. The method of claim 1, wherein the inorganic material has a specific heat capacity of less than about 1.5 J/g K.

11. The method of claim 1, wherein the inorganic material has a conductivity of between about 0.004 W/m·K and about 450 W/m·K.

12. The method of claim 1, wherein the inorganic material has a density of greater than about 1.5 g per cubic centimeter.

13. The method of claim 1, wherein the inorganic material comprises particles having an average particle size of from about 0.1 micron to about 100 microns.

14. The method of claim 1, wherein the combination includes about 0.05 to about 35 percent by weight inorganic material.

15. The method of claim 1, further comprising, after irradiating the combination, converting the irradiated hydrocarbon-containing material in the irradiated combination to a product using an enzyme and/or a microorganism.

16. The method of claim 15, further comprising removing the inorganic material from the irradiated combination.

17. The method of claim 16, further comprising subjecting the irradiated combination to catalytic cracking.

18. The method of claim 1, further comprising refining the hydrocarbon-containing material.

19. The method of claim 1, further comprising extracting a hydrocarbon from the irradiated combination, producing an extracted hydrocarbon.

20. The method of claim 1, wherein a lower molecular weight hydrocarbon component is produced in the irradiated combination from a higher molecular weight hydrocarbon component in the hydrocarbon-containing material.

21. The method of claim 20, wherein the lower molecular weight hydrocarbon is selected from the group consisting of methane, ethane, propane, hexane and mixtures thereof.

22. The method of claim 1, further comprising subjecting the hydrocarbon-containing material to catalytic cracking.

23. The method of claim 1, further comprising subjecting the hydrocarbon-containing material to alkylation.

24. The method of claim 1, further comprising refining the irradiated combination.

25. The method of claim 1, wherein the accelerated charged particles have energies of from 10 to 1000 MeV/atomic unit.

* * * * *